(12) United States Patent
Birdsall et al.

(10) Patent No.: US 9,283,305 B2
(45) Date of Patent: Mar. 15, 2016

(54) HOLLOW TUBULAR DRUG ELUTING MEDICAL DEVICES

(75) Inventors: Matthew J. Birdsall, Santa Rosa, CA (US); Christopher Storment, Sonoma, CA (US); D. H. Perkins, Santa Rosa, CA (US); Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1036 days.

(21) Appl. No.: 12/500,359

(22) Filed: Jul. 9, 2009

(65) Prior Publication Data

US 2011/0008405 A1    Jan. 13, 2011

(51) Int. Cl.
 *A61L 27/54* (2006.01)
 *A61L 31/02* (2006.01)
 *A61L 31/16* (2006.01)

(52) U.S. Cl.
 CPC ............ *A61L 31/022* (2013.01); *A61L 31/16* (2013.01)

(58) Field of Classification Search
 None
 See application file for complete search history.

(56) References Cited

U.S. PATENT DOCUMENTS

| | | |
|---|---|---|
| 2,153,936 A | 4/1939 | Owens et al. |
| 4,531,933 A | 7/1985 | Norton et al. |
| 4,643,716 A | 2/1987 | Drach |
| 4,720,384 A | 1/1988 | DiLuccio et al. |
| 4,763,647 A | 8/1988 | Gambale |
| 4,800,082 A | 1/1989 | Karbowski et al. |
| 4,800,882 A | 1/1989 | Gianturco |
| 4,813,925 A | 3/1989 | Anderson, Jr. et al. |
| 4,886,062 A | 12/1989 | Wiktor |
| 4,913,683 A | 4/1990 | Gregory |
| 5,019,090 A | 5/1991 | Pinchuk |
| 5,063,935 A | 11/1991 | Gambale |
| 5,133,732 A | 7/1992 | Wiktor |
| 5,154,705 A | 10/1992 | Fleishhacker et al. |
| 5,234,456 A | 8/1993 | Silvestrini |
| 5,306,250 A | 4/1994 | March et al. |
| 5,345,945 A | 9/1994 | Hodgson et al. |
| 5,536,274 A | 7/1996 | Neuss |
| 5,538,735 A | 7/1996 | Ahn |
| 5,569,197 A | 10/1996 | Helmus et al. |
| 5,605,162 A | 2/1997 | Mirzaee et al. |
| 5,630,840 A | 5/1997 | Mayer |
| 5,670,161 A | 9/1997 | Healy et al. |
| 5,782,903 A | 7/1998 | Wiktor |
| 5,795,318 A | 8/1998 | Wang et al. |
| 5,824,045 A | 10/1998 | Alt |
| 5,843,117 A | 12/1998 | Alt et al. |
| 5,882,335 A | 3/1999 | Leone et al. |
| 5,891,108 A | 4/1999 | Leone et al. |
| 5,902,266 A | 5/1999 | Leone et al. |
| 5,957,903 A | 9/1999 | Mirzaee et al. |
| 6,022,369 A | 2/2000 | Jacobsen et al. |
| 6,063,101 A | 5/2000 | Jacobsen et al. |
| 6,071,305 A | 6/2000 | Brown et al. |
| 6,099,561 A | 8/2000 | Alt |
| 6,136,023 A * | 10/2000 | Boyle ........................ 623/1.22 |
| 6,248,190 B1 | 6/2001 | Stinson |
| 6,358,276 B1 | 3/2002 | Edwin |
| 6,478,778 B1 | 11/2002 | Jacobsen et al. |
| 6,497,709 B1 | 12/2002 | Heath |
| 6,558,422 B1 | 5/2003 | Baker et al. |
| 6,623,519 B2 | 9/2003 | Edwin et al. |
| 6,641,607 B1 | 11/2003 | Hossainy et al. |
| 6,656,162 B2 | 12/2003 | Santini, Jr. et al. |
| 6,699,281 B2 | 3/2004 | Vallana et al. |
| 6,752,829 B2 | 6/2004 | Kocur et al. |
| 6,783,543 B2 | 8/2004 | Jang |
| 6,989,071 B2 | 1/2006 | Kocur et al. |
| 7,037,330 B1 * | 5/2006 | Rivelli et al. ................ 623/1.15 |
| 7,041,130 B2 | 5/2006 | Santini, Jr. et al. |
| 7,044,965 B1 | 5/2006 | Spielberg |
| 7,060,093 B2 | 6/2006 | Dang et al. |
| 7,101,392 B2 | 9/2006 | Heath |
| 7,122,048 B2 | 10/2006 | Dimatteo et al. |
| 7,135,039 B2 | 11/2006 | De Scheerder et al. |
| 7,182,735 B2 | 2/2007 | Shireman et al. |
| 7,288,084 B2 | 10/2007 | Li |
| 7,316,565 B2 | 1/2008 | Liao |
| 7,344,563 B2 | 3/2008 | Vallana et al. |
| 7,384,660 B2 | 6/2008 | Hossainy et al. |
| 7,400,931 B2 | 7/2008 | Mandrusov et al. |
| 7,419,681 B2 | 9/2008 | Tormala et al. |

(Continued)

FOREIGN PATENT DOCUMENTS

| | | |
|---|---|---|
| EP | 836839 A2 | 10/1997 |
| EP | 1600534 | 11/2005 |

(Continued)

OTHER PUBLICATIONS

U.S. Appl. No. 09/716,146, filed Nov. 17, 2000, Boyle.
Basarir et al., "Osseointegration in Arthroplasty: Can Simvastatin Promote Bone Response to Implants?" International Orthopaedics (SICOT)(2009) 33:855-859.
U.S. Appl. No. 12/428,581, filed Apr. 23, 2009, Hoff et al.
U.S. Appl. No. 12/500,359, filed Jul. 9, 2009, Storment et al.

(Continued)

*Primary Examiner* — Tigabu Kassa

(57) ABSTRACT

A method of a forming a hollow, drug-eluting medical device includes providing composite member having an outer member and a core member disposed within a lumen of the outer member. The composite member is shaped into a pattern. Openings are formed through the outer member of the composite member. The composite member is processed to remove the core member from the lumen of the outer member without harming the outer member, leaving a hollow tubular member already formed into the desired pattern. The lumen of the outer member is filled with a therapeutic substance.

20 Claims, 12 Drawing Sheets

(56) References Cited

U.S. PATENT DOCUMENTS

| | | |
|---|---|---|
| 7,455,667 B2 | 11/2008 | Uhland et al. |
| 7,575,593 B2 | 8/2009 | Rea et al. |
| 2002/0065548 A1 | 5/2002 | Birdsall et al. |
| 2002/0087209 A1 | 7/2002 | Edwin et al. |
| 2002/0103527 A1 | 8/2002 | Kocur et al. |
| 2002/0138048 A1 | 9/2002 | Tuch |
| 2003/0021825 A1 | 1/2003 | Pathak et al. |
| 2003/0068353 A1 | 4/2003 | Chen et al. |
| 2003/0125803 A1 | 7/2003 | Vallana et al. |
| 2003/0208256 A1 | 11/2003 | DiMatteo et al. |
| 2004/0006382 A1 | 1/2004 | Sohier |
| 2004/0024449 A1 | 2/2004 | Boyle |
| 2004/0037889 A1 | 2/2004 | Richeal et al. |
| 2004/0106984 A1 | 6/2004 | Stinson |
| 2004/0133270 A1 | 7/2004 | Grandt |
| 2004/0148012 A9 | 7/2004 | Jang |
| 2005/0043783 A1 | 2/2005 | Amis et al. |
| 2005/0055080 A1 | 3/2005 | Istephanous et al. |
| 2005/0060020 A1 | 3/2005 | Jenson |
| 2005/0070996 A1 | 3/2005 | Dinh et al. |
| 2005/0080481 A1 | 4/2005 | Madda et al. |
| 2005/0145307 A1 | 7/2005 | Shireman et al. |
| 2005/0177226 A1 | 8/2005 | Banik et al. |
| 2005/0186241 A1 | 8/2005 | Boyle et al. |
| 2005/0208100 A1 | 9/2005 | Weber et al. |
| 2005/0272806 A1 | 12/2005 | Falotico et al. |
| 2005/0278016 A1 | 12/2005 | Welsh et al. |
| 2006/0004437 A1 | 1/2006 | Jayaraman |
| 2006/0064157 A1 | 3/2006 | Shanley |
| 2006/0122689 A1 | 6/2006 | Kocur et al. |
| 2006/0129231 A1 | 6/2006 | De Scheerder et al. |
| 2006/0147489 A1 | 7/2006 | Shanley et al. |
| 2006/0155369 A1 | 7/2006 | Edwin et al. |
| 2006/0212109 A1 | 9/2006 | Sirhan et al. |
| 2006/0224234 A1 | 10/2006 | Jayaraman |
| 2006/0224237 A1 | 10/2006 | Furst et al. |
| 2007/0005124 A1 | 1/2007 | De Scheerder et al. |
| 2007/0027531 A1 | 2/2007 | Dimatteo et al. |
| 2007/0043423 A1 | 2/2007 | Grewe |
| 2007/0055352 A1 | 3/2007 | Naimark et al. |
| 2007/0061007 A1 | 3/2007 | Nolting |
| 2007/0112417 A1 | 5/2007 | Shanley et al. |
| 2007/0123805 A1 | 5/2007 | Shireman et al. |
| 2007/0168021 A1 | 7/2007 | Holmes, Jr. et al. |
| 2007/0173923 A1 | 7/2007 | Savage et al. |
| 2007/0219628 A1 | 9/2007 | Shanley et al. |
| 2007/0282419 A1 | 12/2007 | Hilaire et al. |
| 2008/0003251 A1 | 1/2008 | Zhou |
| 2008/0051882 A1 | 2/2008 | Rubin |
| 2008/0065201 A1 | 3/2008 | Li |
| 2008/0077233 A1 | 3/2008 | Diaz et al. |
| 2008/0183281 A1 | 7/2008 | Rea et al. |
| 2008/0188925 A1 | 8/2008 | Zhao |
| 2008/0195170 A1* | 8/2008 | Asgari .......................... 607/36 |
| 2008/0195196 A1 | 8/2008 | Asgari |
| 2008/0234809 A1 | 9/2008 | Greenan |
| 2008/0249599 A1 | 10/2008 | Allen et al. |
| 2008/0255659 A1 | 10/2008 | Huang et al. |
| 2008/0276935 A1 | 11/2008 | Wang |
| 2008/0306579 A1 | 12/2008 | Dolan et al. |
| 2009/0024209 A1 | 1/2009 | Ozdil et al. |
| 2009/0024210 A1 | 1/2009 | Klocke et al. |
| 2009/0035351 A1 | 2/2009 | Berglund et al. |
| 2009/0061071 A1 | 3/2009 | McMorrow et al. |
| 2009/0093871 A1 | 4/2009 | Rea et al. |
| 2009/0132031 A1 | 5/2009 | Cook et al. |
| 2009/0157172 A1 | 6/2009 | Kokate et al. |
| 2009/0163995 A1 | 6/2009 | Shanley et al. |
| 2009/0192593 A1 | 7/2009 | Meyer et al. |
| 2009/0220612 A1 | 9/2009 | Perera |
| 2009/0228095 A1 | 9/2009 | Shanley et al. |
| 2009/0281615 A1 | 11/2009 | Kocur et al. |
| 2009/0312833 A1 | 12/2009 | Tittelbach et al. |
| 2009/0319026 A1 | 12/2009 | Meyer |
| 2010/0010621 A1 | 1/2010 | Klocke |
| 2010/0023115 A1 | 1/2010 | Robaina et al. |
| 2010/0036482 A1 | 2/2010 | Svrluga et al. |
| 2010/0057196 A1 | 3/2010 | Pathak |
| 2010/0070022 A1 | 3/2010 | Kuehling |
| 2010/0082096 A1 | 4/2010 | Gregorich |
| 2010/0145437 A1 | 6/2010 | Girton et al. |

FOREIGN PATENT DOCUMENTS

| | | |
|---|---|---|
| EP | 836839 B1 | 7/2006 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO02/060506 | 8/2002 |
| WO | WO03/092547 | 11/2003 |
| WO | WO2007/021749 | 2/2007 |

OTHER PUBLICATIONS

Polacco et al. "Biodegradable Hollow Fibres Containing Drug-Loaded Nanoparticles as Controlled Release Systems" Polym International 51:1464-1472 (2002).

Derle et al., "Particle Engineering Techniques to Enhance Dissolution of Poorly Water Soluble Drugs" International Journal of Current Pharmaceutical Research, vol. 2, Issue 1, 2010, pp. 10-15.

Purvis et al., "Cryogenic Liquids, Nanoparticles, and Microencapsulation" International Journal of Pharmaceutics, 2006.

"Breakthrough Solubilization Technology Targets Stubborn Drug Candidates" Dowpharma.

"Supercritical Carbon-Dioxide Cleaning Defined" Supercritical Carbon-Dioxide Cleaning Technology Review, Jul. 1996.

Berger "Coating Drug-Eluting Arterial Stents Using Ultrasonic Spray Nozzle" ILASS Americas, 19th Annual Conference on Liquid Atomization and Spray Systems, May 2006.

PCT Search Report PCT/US2010/039087.
PCT Search Report PCT/US2010/049439.
PCT Search Report PCT/US2010/049437.
PCT Search Report PCT/US2010/049434.

* cited by examiner

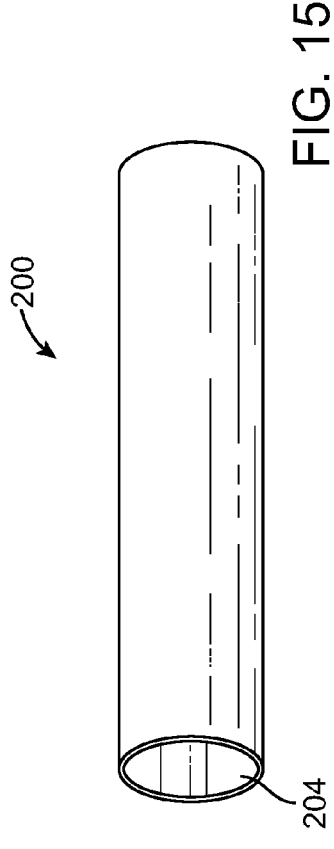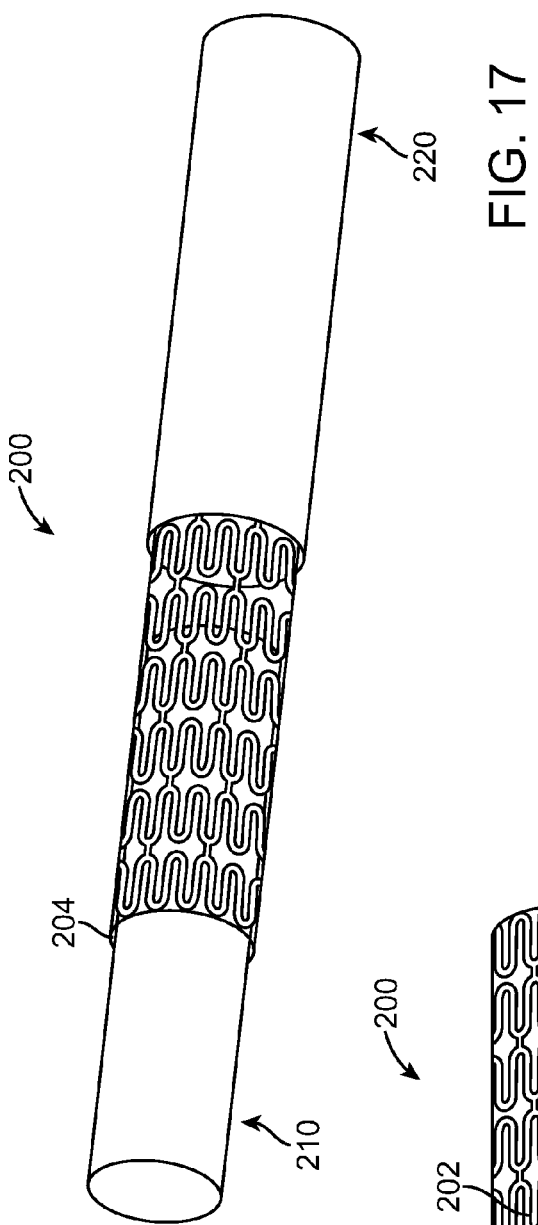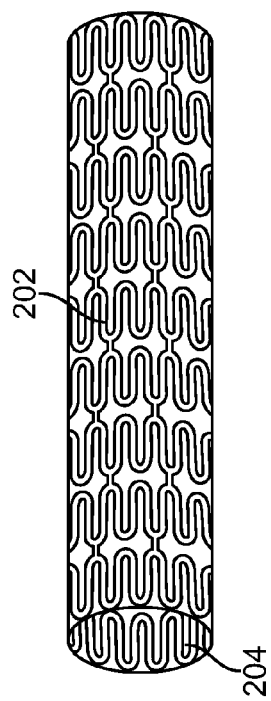

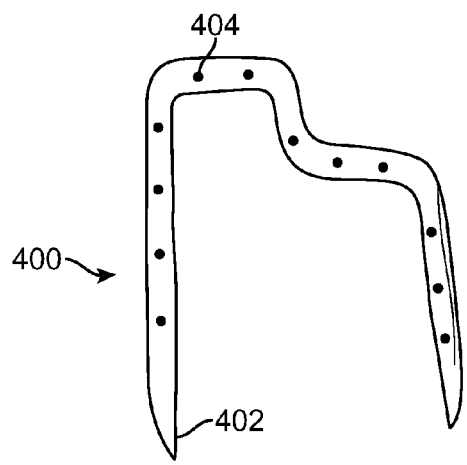
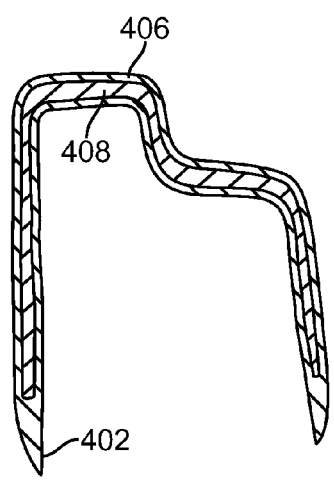
FIG. 29　　　　　FIG. 31
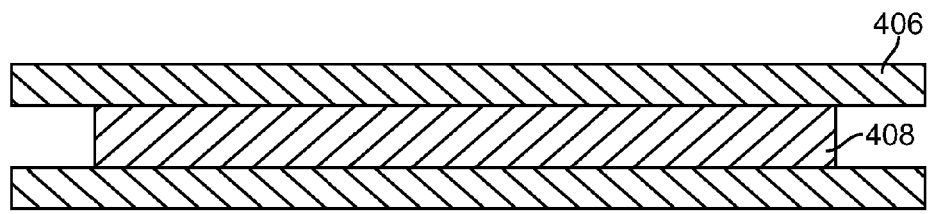
FIG. 30
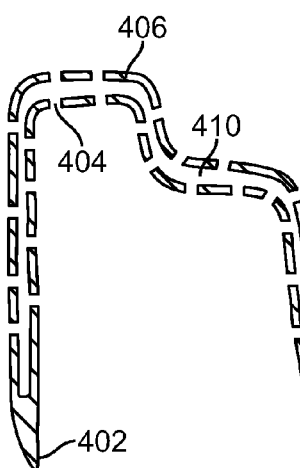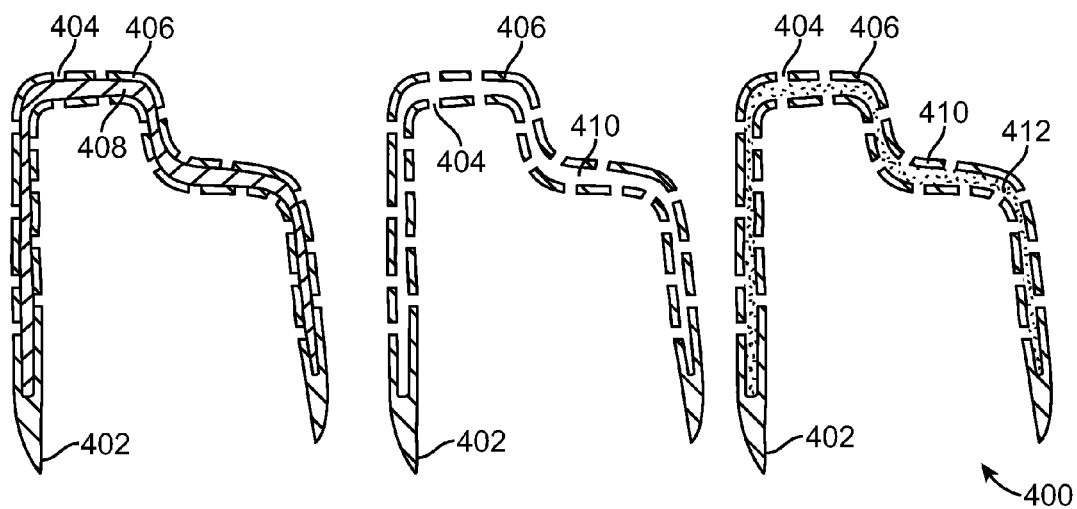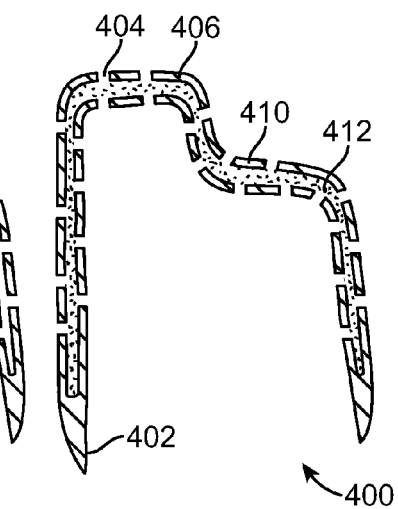
FIG. 32　　　FIG. 33　　　FIG. 34

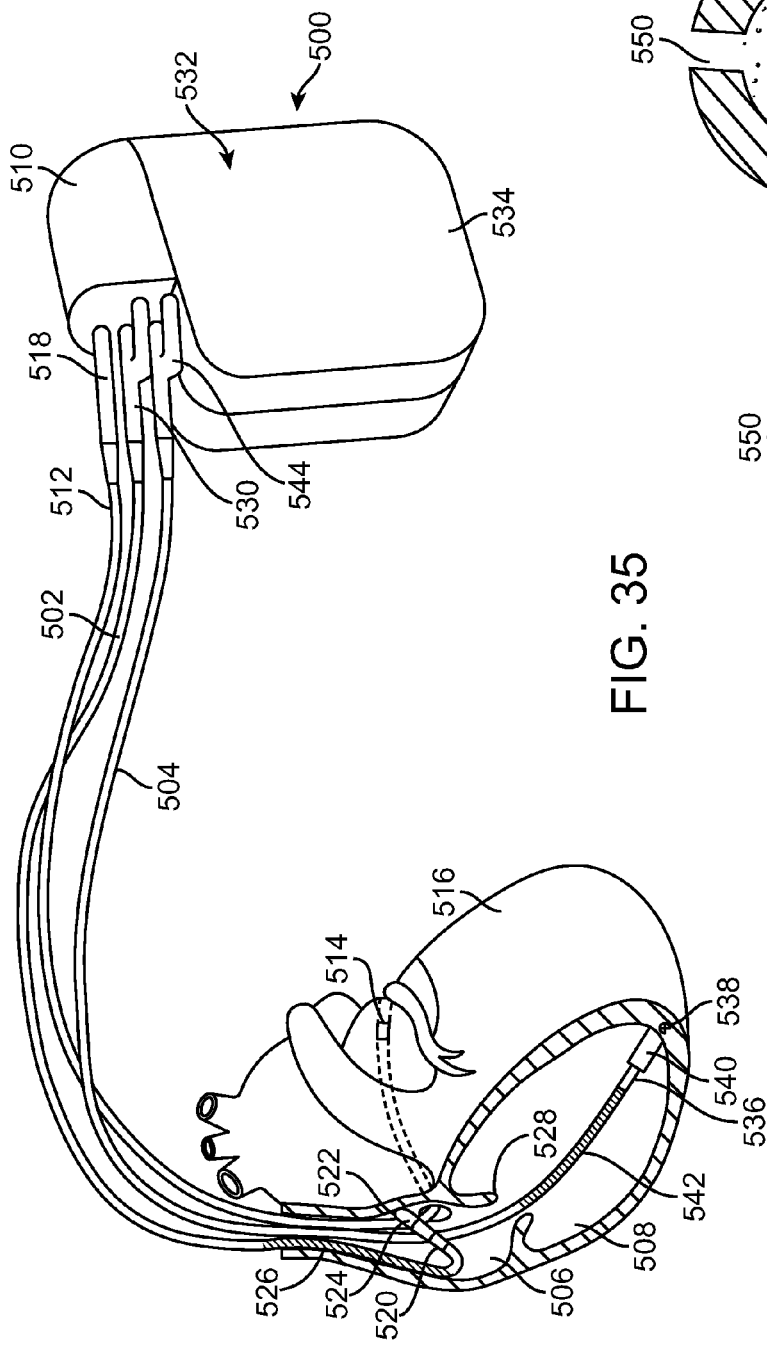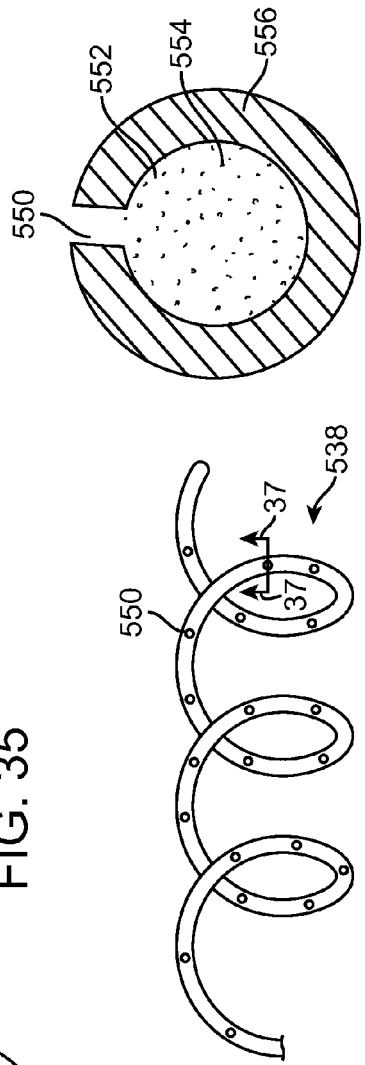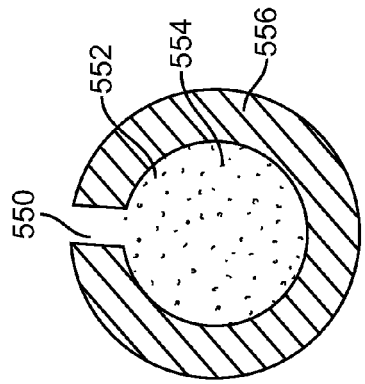

HOLLOW TUBULAR DRUG ELUTING MEDICAL DEVICES

FIELD OF THE INVENTION

The present invention relates to implantable medical devices that release a therapeutic substance and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Similarly, therapeutic agents have been added to orthopedic devices such a joint replacement prostheses, bone screws, staples and the like. Risks that may follow the placement of such devices include infection and, in the long term with some types of devices, loss of bone tissue at the interface with the device as the bone remodels and consequent loosening of the device. Therapeutic agents in such orthopedic devices may promote and/or inhibit bone and/or other tissue growth, inhibit rejection of the device or of components connected to or located adjacent to the device, reduce infection, reduce inflammation, reduce pain, provide vitamins and/or minerals, promote healing of surrounding tissue, and other similar functions.

Surgical staples have also included therapeutic agents to assist healing, prevent infections, or prevent other possible harmful effects of the surgical staple. Agents such as antimicrobial agents, anticoagulants, antithrombotic agents, antiplatelet agents, antiproliferative agents, anti-inflammatory agents, lipid-lowering agents, specific growth factor antagonists, antioxidants, genetic materials, angiogenic growth factors, antihypertension drugs, radioactive compounds, lymphokines, and other suitable agents have been proposed.

Leads connected to implantable cardioverter defibrillators are positioned inside the heart or on its surface. These leads are used to deliver electrical shocks, sense the cardiac rhythm and sometimes pace the heart, as needed. At the end of the leads are spiral wound metallic electrodes that are placed into the heart tissue, and deliver the electrical stimulation to the heart. It has been found that the natural immune response to a foreign body in tissue generate chemical species (typically peroxy compounds) that greatly increase corrosion of the metallic electrode. To thwart this immune response and the associated corrosion, electrodes are coated with anti-inflammatory drugs such as steroids, antibiotics, anti-fungal materials and the like by spray or dip coating methods. However, such coatings may be damaged during delivery to and insertion into the heart tissue. Further, it is sometimes difficult to deliver precise dosages of the drug.

The drug-eluting medical devices discussed above may be coated with a polymeric material which, in turn, is impregnated with a drug or a combination of drugs. Once the medical device is implanted at a target location, the drug(s) is released from the polymer for treatment of the local tissues. The drug(s) is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Accordingly, drug-eluting medical devices that enable increased quantities of a drug to be delivered by the medical device, and allow for improved control of the elution rate of the drug, and improved methods of forming such medical devices are needed.

BRIEF SUMMARY OF THE INVENTION

Hollow, drug-eluting medical devices and methods of forming hollow, drug-eluting medical devices are disclosed. In an embodiment a core wire or composite member having an outer member and a core member disposed within a lumen of the outer member is shaped into the medical device. Openings are formed through the outer member of the core wire. The core wire is exposed to an etchant that removes the core member but does not harm the outer member, leaving a hollow tubular wire. The lumen of the outer member is filled with a therapeutic substance. Medical devices for which the method can be used include stents, bone screws, staples, and implantable cardioverter defibrillators.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 15-22 show a method of forming a stent according to another embodiment hereof.

FIG. 29 is a schematic illustration of a hollow, drug-eluting staple in accordance with an embodiment hereof.

FIGS. 30-34 are cross-sectional views of a method of forming the hollow, drug-eluting staple of FIG. 29.

FIG. 35 is a schematic illustration of an implantable cardioverter defibrillator.

FIGS. 36 and 37 show an electrode for use with an implantable cardioverter defibrillator.

DETAILED DESCRIPTION OF THE INVENTION

Figure 1:
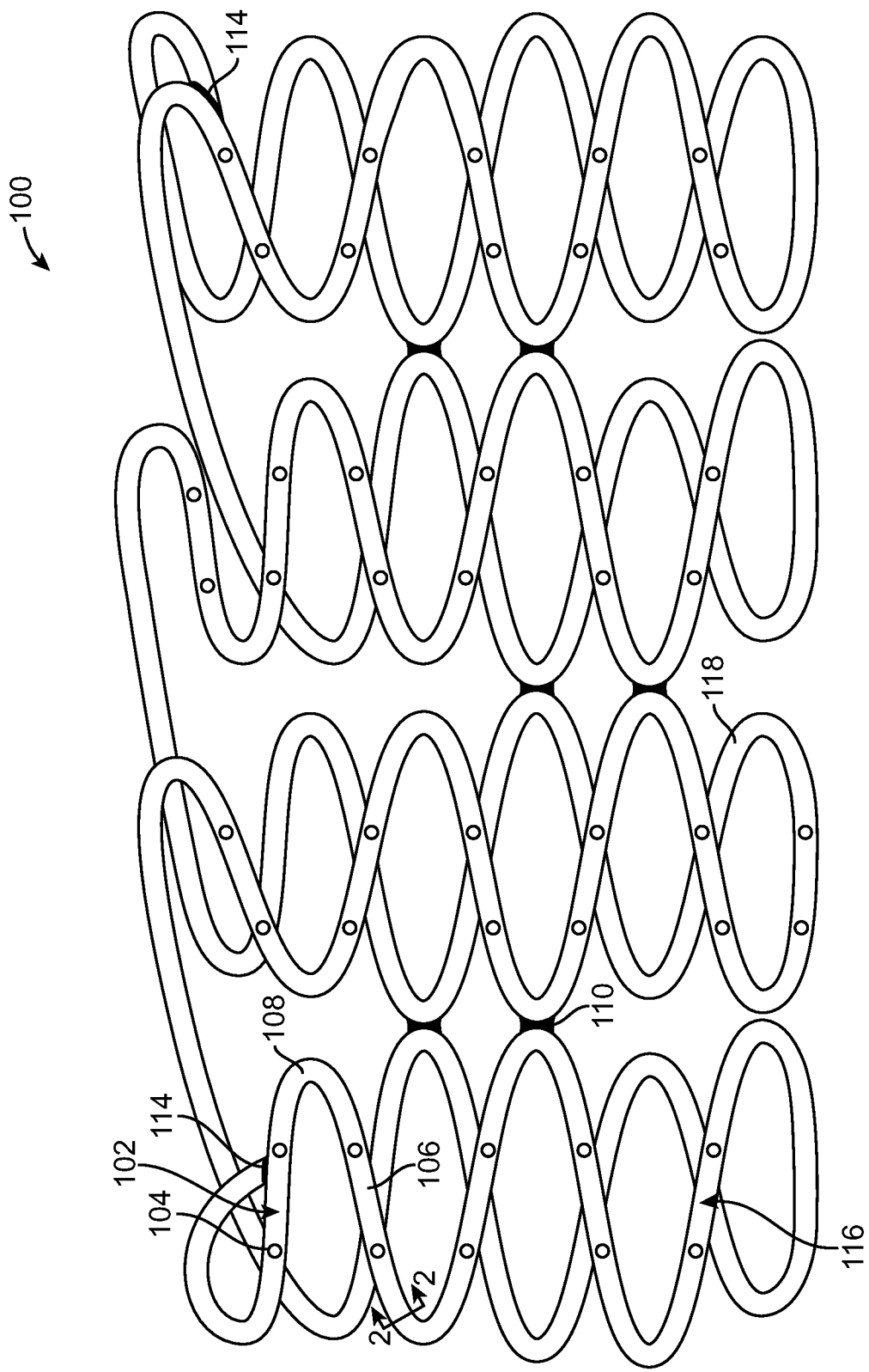
FIG. 1 is a schematic illustration of an exemplary stent in accordance with an embodiment hereof.
Figure 2:
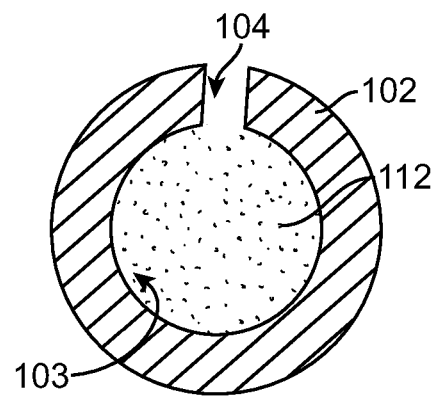
FIG. 2 is a cross-sectional view taken along line 2-2 of FIG. 1.
Figure 3:
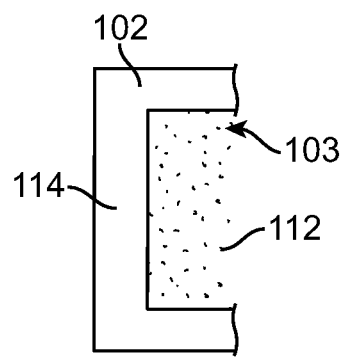
FIG. 3 is a longitudinal cross-section of an end of the wire of the stent of FIG. 1.
Figure 4:
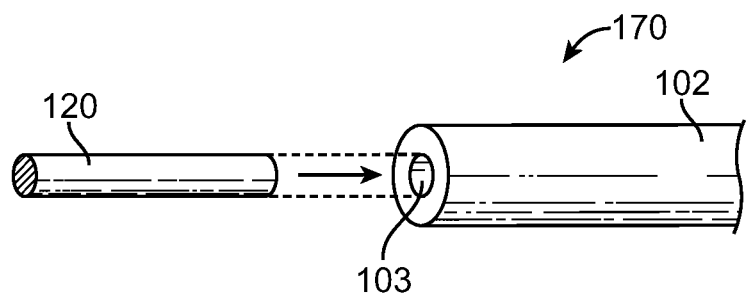
FIG. 4 is a schematic illustration of a core wire.

Specific embodiments of the present invention are now described with reference to the figures, where like reference numbers indicate identical or functionally similar elements.
Stent Embodiments An embodiment of a stent 100 disclosed herein is shown in FIGS. 1-3. In particular, stent 100 is formed from a hollow wire 102. In the embodiment shown in FIG. 1, stent 100 is formed into a series of generally sinusoidal waves including generally straight segments 106 joined by bent segments or crowns 108 and form a generally tubular stent 100. The generally sinusoidal pattern is formed into a tube, as shown in FIG. 1. In the embodiment shown in FIG. 1, selected crowns 108 of longitudinally adjacent sinusoids may be joined by, for example, welds 110. The invention hereof is not limited to the pattern shown in FIG. 1. Stent 100 can be formed into any pattern suitable for use as a stent. For example, and not by way of limitation, stent 100 can be formed into patterns disclosed in U.S. Pat. No. 4,800,082 to Gianturco, U.S. Pat. No. 4,886, 062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety.

As shown in FIG. 2, hollow wire 102 of stent 100 allows for a therapeutic substance or drug 112 to be deposited within the lumen 103 of hollow wire 102. Although hollow wire 102 is shown as generally having a circular cross-section, hollow wire 102 may be generally elliptical or rectangular in cross-section. Hollow wire 102 further includes cuts or openings 104 dispersed along its length to permit drug 112 to be released from lumen 103. Openings 104 may be disposed only on generally straight segments 106 of stent 100, only on crowns 108 of stent 100, or both generally straight segments 106 and crowns 108. Openings 104 may be sized and shaped as desired to control the elution rate of drug 112 from stent 100. Larger sized openings 104 generally permit a faster elution rate and smaller sized openings 104 generally provide a slower elution rate. Further, the size and/or quantity of openings 104 may be varied along stent 100 in order to vary the quantity and/or rate of drug 112 being eluted from stent 100 at different portions of stent 100. Openings 104 may be, for example and not by way of limitation, 10-30 μm in diameter. Openings 104 may be provided only on an outwardly facing or ablumenal surface 116 of stent 100, as shown in FIG. 2, only on the inwardly facing or lumenal surface 118 of stent 100, both surfaces, or may be provided anywhere along the circumference of wire 102.

Ends 114 of wire 102 may be closed, as shown in FIG. 3. Ends 114 may be closed by crimping excess material of wire 102 to close lumen 103. Closing ends 114 prevents drug 114 from prematurely releasing from ends 114. However, closing ends 114 is not required as drug 112 may be dried, provided within a polymer matrix, enclosed within a liner (not shown), or otherwise protected from premature release from ends 114. Further, ends 114 may be welded, crimped or otherwise connected to other portions of wire 102 such that the ends 114 are not free ends. Ends 114 may alternatively be provided as free ends.

Figure 8:
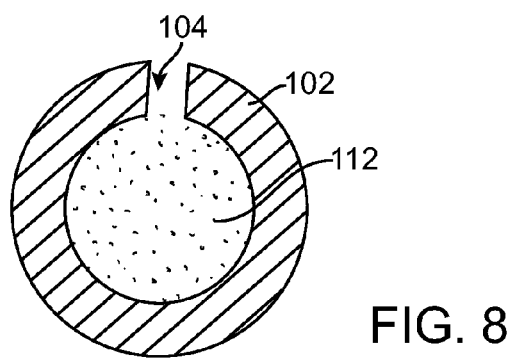
Figure 9:
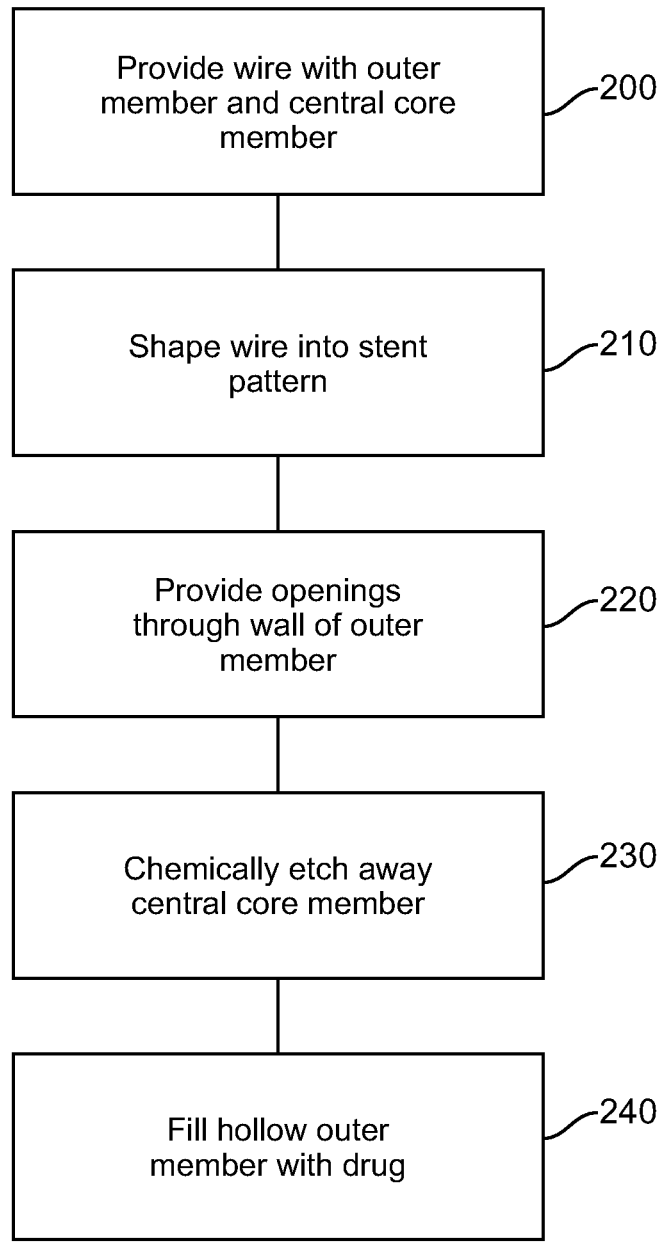
FIG. 9 is a flow chart illustrating a method of forming a hollow wire in accordance with an embodiment hereof.

FIGS. 4-9 show a method for forming a hollow wire stent in accordance with an embodiment hereof. As shown in FIG. 9, step 200 is to provide a wire with an outer member and a central core member. These types of wire are sometimes referred to as core wires and may as be referred to as composite members. Core wire 170 hereof is formed of an outer member 102 and an inner or core member 120, as shown schematically in FIG. 4. Outer member 102 becomes hollow wire 102 of stent 100, and thus has been labeled with the same reference number. Core wire 170 may be formed by any method known in the art, for example and not by way of limitation, a drawn filled tubing process, extruding the outer member over the inner member, or any other suitable method. Examples of core wires and methods of forming core wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 102 can be any material that is suitable to be used as a stent. Outer member 102, as explained in more detail below, is the surviving material that will become hollow wire 102. For example and not by way of limitation, outer member 102 may be a stainless steel, "MP35N," "MP20N," nickel titanium alloys such as Nitinol, magnesium, L605, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The requirements for the material of outer member 102 are that it be biocompatible, sufficiently resilient to be used as a stent, and that it survives the process for eliminating core member 120, as discussed in more detail below.

Core member 120 may be a material that provides sufficient support to outer member 102 while the core wire is being bent into the stent pattern, as explained in more detail below. Core member 120 may be made of a material that is more ductile than the material of outer member 102 or may have a higher melting point than the material of outer member 102. Further, core member 120 is made of a sacrificial material that can be removed by a process that does not damage the material of outer member 102. Examples of materials for core member 102 include, but are not limited to, tungsten (W), molybdenum (Mo), niobium (Nb), rhenium (Re), carbon (C), germanium (Ge), silicon (Si) and alloys thereof.

Figure 5:
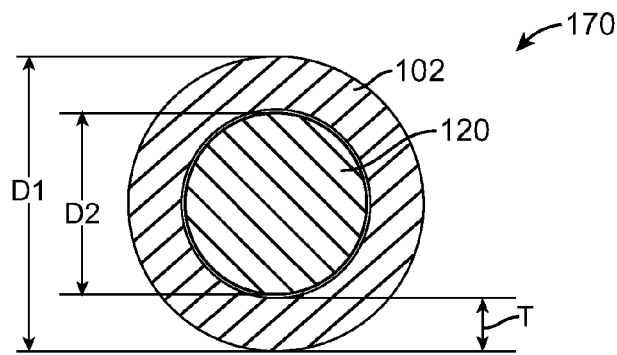
FIGS. 5-8 are a cross-sectional views showing the steps of forming a hollow wire in accordance with an embodiment hereof.

A cross-section of core wire 170 is shown in FIG. 5. Outer member 102 may have an outer diameter $D_1$ in the range of 0.0025 inch to 0.010 inch and wall thickness T in the range of 0.0005 inch or larger, depending on the application, for example, in what lumen or organ and for what purpose the stent is to be utilized. The values listed above are merely examples and other diameters and thicknesses may be used depending on, for example, the material used, the desired stent shape, and the purpose or location of the stent.

Referring to FIG. 9, step 210 is to shape the core wire 170 into the stent pattern. As discussed above, the stent pattern can be the pattern shown in FIG. 1 or any other suitable pattern formed from a wire. Further, although the order of all the steps is not critical, step 210 must be done prior to removing core member 120, as explained in more detail below. Shaping core wire 170 into the stent pattern while core member 120 is disposed within outer member 102 helps prevent kinking or other deformations from occurring in outer member 102. Shaping the core wire 170 into the stent pattern shown in FIG. 1 generally includes the steps of forming core wire 170 into a two dimensional sinusoid pattern followed by wrapping the pattern around a mandrel, as known to those skilled in the art. The end result is a helical stent pattern formed onto a mandrel. Selected crowns 108 of the helical pattern are then welded together and the stent is removed from the mandrel.

Figure 6:
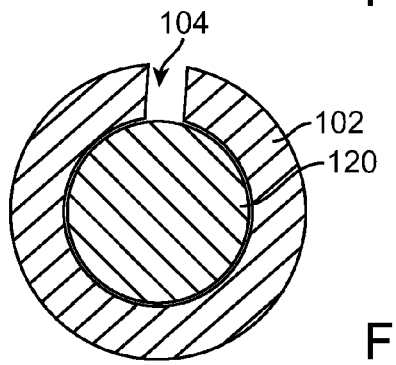
Figure 7:
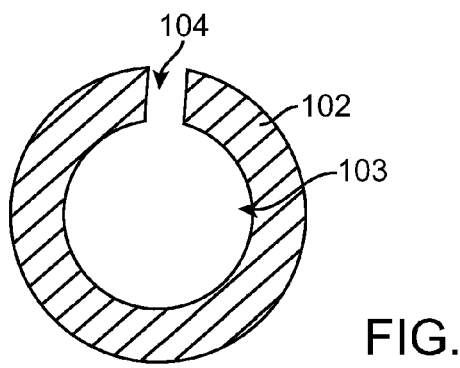

Step 220 shown in FIG. 9 is to provide openings 104 in outer member 102. Openings 104 may be laser cut, drilled, etched, or otherwise provided in outer member 102. Step 220 need not be performed after step 210, nor before step 230, although it is preferred to be before step 230, as explained in more detail below. If step 220 is performed after step 210, a cross-section of core wire 170 will include outer member 102, inner member 120, and an opening 104, as shown in FIG. 6.

Step 230 is to chemically etch away core member 120. Step 230 can be performed by any suitable process for removing core member 120 while preserving outer member 102. In particular, subjecting core wire 170 to xenon difluoride ($XeF_2$) gas at low pressure 1-6 Torr and relatively high temperature (approximately 150° C.) causes the xenon difluoride ($XeF_2$) gas to react with a tantalum (Ta) core member 102 to form $TaF_5$ and Xe gases, which can be exhausted from lumen 103. Xenon difluoride ($XeF_2$) gas reacts similarly with a core member 120 made from tungsten, molybdenum, niobium, rhenium, carbon, germanium, and silicon. However, xenon difluoride ($XeF_2$) gas does not react with an outer member formed of MP35N. Accordingly, after step 230 is completed, outer member 102 remains and core member 120 has been removed, leaving the structure shown in FIG. 7. As noted above, openings 104 do not need to be formed prior to the step of removing core member 120 as long as there is a way to expose core member 120 to the etchant. For example, ends 114 of the wire may be open or temporary ports may for formed through outer member 102 to expose core member 120 to the etchant.

Figure 10:
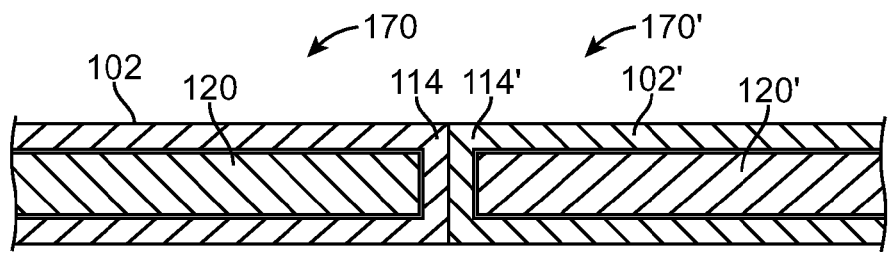
FIGS. 10-13 are longitudinal cross-sectional views showing the steps of forming a hollow wire from two core wires in accordance with an embodiment hereof.

After core member 120 has been removed, drug 112 may be injected into lumen 103 of outer member 102, as shown in step 240 of FIG. 10. This produces a hollow wire or outer member 102 with drug 112 disposed in lumen 103 thereof, and openings 104 through which drug 112 may be eluted, as shown in FIGS. 2 and 8.

Stent 100 may be used conventionally in blood vessels of the body to support such a vessel after an angioplasty procedure. It is known that certain drugs eluted from stents may prevent restenosis or other complications associated with angioplasty or stents. Stent 100 may alternatively be used in other organs or tissues of the body for delivery of drugs to treat tumors, inflammation, nervous conditions, or other conditions that would be apparent to those skilled in the art.

FIGS. 10-13 show another embodiment of a hollow wire used to form a stent, wherein the hollow wire is formed from a first core wire 170 and a second core wire 170' coupled to each other in an end to end fashion. Only a portion of the wires are shown in FIGS. 10-13. Further, more than two wires may be coupled to each other to form a stent as disclosed herein.

As shown in FIG. 10, a distal end 114 of first core wire 170 is coupled to a proximal end 114' of second core wire 170'. First core wire 170 includes a first outer member 102 and a first core member 120 disposed within a first lumen 103 of first outer member 102. Similarly, second core wire 170' includes a second outer member 102' and a second core member 120' disposed within a second lumen 103' of outer member 102'. First core wire 170 and second core wire 170' may be coupled together through welding, soldering, adhesives, mechanical coupling, or other means known to those skilled in the art.

Figure 11:
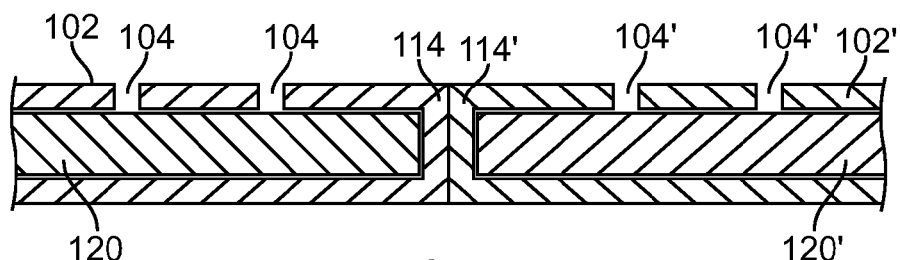

The coupled core wires 170, 170' are then shaped into a stent pattern, such as the pattern shown in FIG. 1. First openings 104 are formed through first outer member 102 of first core wire 170 and second openings 104' are formed through second outer member 102' of second core wire 170', as shown in FIG. 11. First and second openings 104, 104' may be the same size and shape or may be different sizes and/or shapes depending on the application. Openings 104, 104' may be formed as discussed above.

Figure 12:
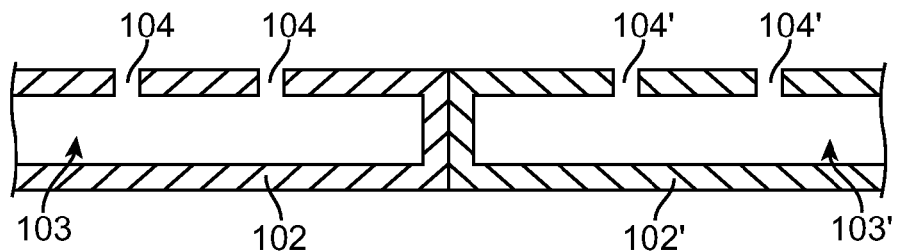

First and second core wires 170, 170' are then exposed to a chemical etchant to remove first core member 120 and second core member 120', leaving the first and second outer members 102, 102', as shown in FIG. 12. The chemical etchant can be as discussed above.

Figure 13:
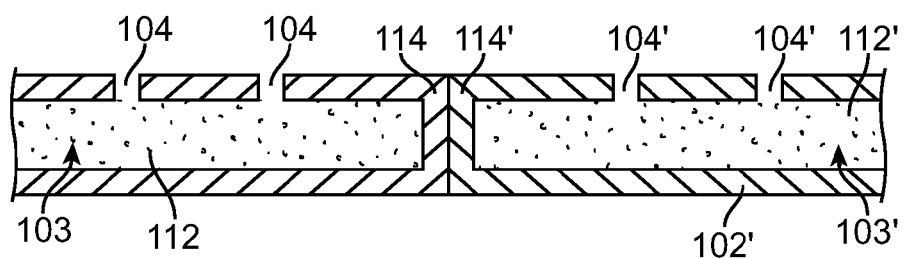

A first drug 112 is then injected into first lumen 103 of first outer member 102 and a second drug is injected into second lumen 103' of second outer member 102', as shown in FIG. 13. First drug 112 and second drug 112' may be different drugs or different concentrations of the same drug, depending on the application.

Figure 14:
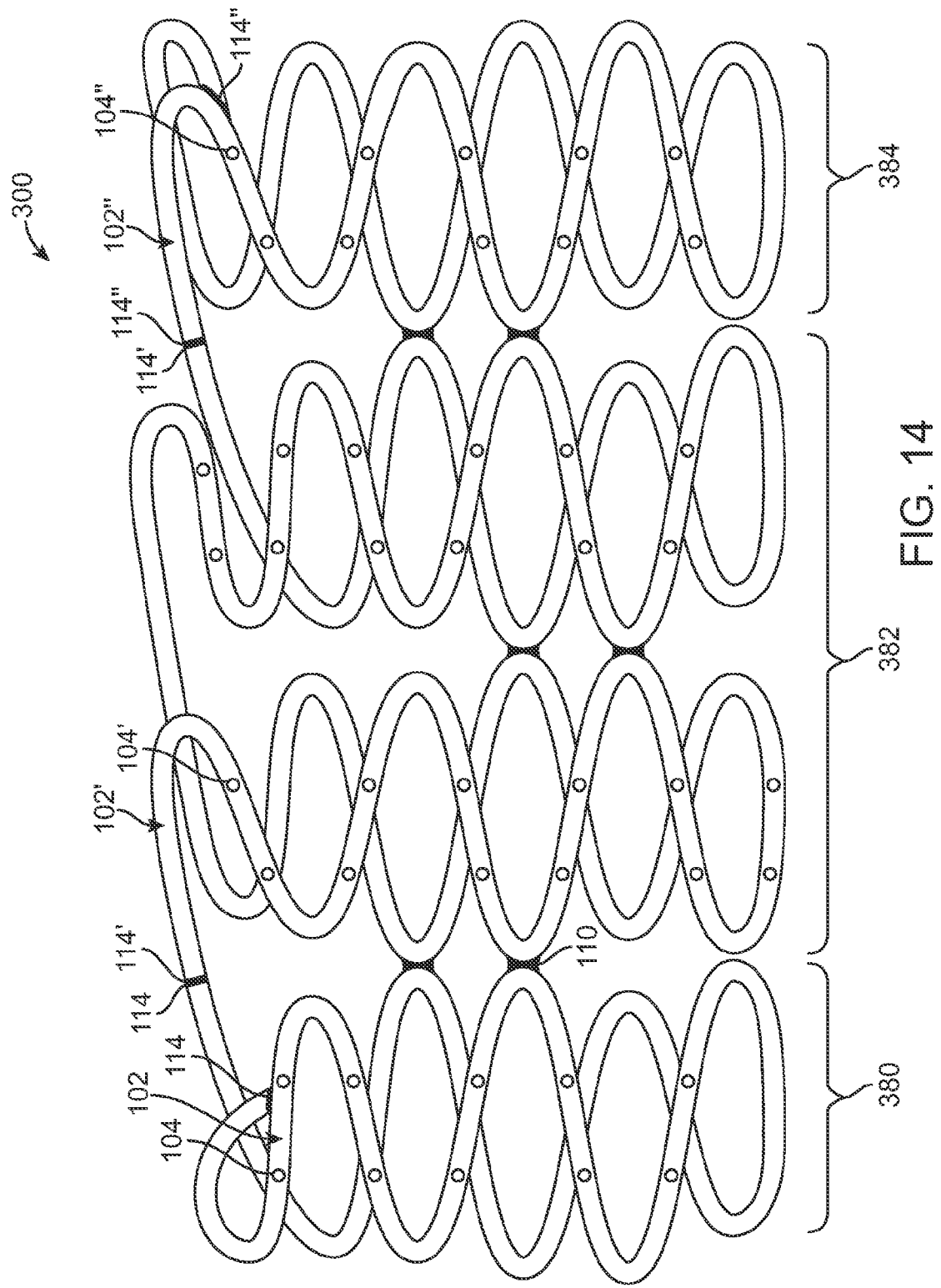
FIG. 14 is a schematic illustration of a stent formed from multiple hollow wires in accordance with another embodiment hereof.

Coupling multiple wires together to form a stent allows different drugs or different dosages of the same drug may be used for different portions of the stent. For example, a stent 300 shown in FIG. 14 may be used to treat a tumor wherein a greater concentration of drug 112 is required at a center portion 382 of stent 300 and lesser concentrations of drug 112 are required at proximal and distal portions 380, 384 of stent 300. Thus, a first core wire, a second wire, and a third wire core wire are coupled together end-to-end (114, 114', 114") as explained above with respect to FIG. 10. The attached core wires are then shaped into a stent, such as the stent shown in FIG. 14. The first core wire is the appropriate length to form proximal portion 380, the second core wire is the appropriate length to form center portion 382, and the third core wire is the appropriate length to form distal portion 384. Holes 104, 104', 104" are formed through outer members 102, 102', 102" of the first, second, and third core wires, respectively. The core wires are exposed to a chemical etchant to remove the core members, as discussed above, and each outer member 102, 102', 102" is filled with a respective drug.

Another method for forming a stent including hollow struts is described referring to FIGS. 15-22. The previous embodiment described have formed a core wire into a stent shape and then removed the core or inner member of the core wire, leaving a hollow wire shaped into a stent form. As understood by those skilled in the art, stents are also manufactured starting with a hollow, generally cylindrical thin-walled tube as shown, and then laser-cutting or etching away material from the tube to leave a generally cylindrical stent. The struts in such a method are the thickness of the wall of the tube. In the method of the present embodiment, such struts are made to be hollow such that the struts can be filled with a therapeutic substance.

In the present embodiment, a generally cylindrical, thin-walled tube 200, shown in FIG. 15, is laser-cut, etched, or otherwise processed to remove material such that the remaining material is in the desired stent shape, as show in FIG. 16. However, tube 200 is made of a sacrificial material similar to materials described herein for the core member of a core wire. Further, struts 202 remaining from tube 200 are sized and spaced not as the final stent struts. Instead, struts 202 are sized and spaced as the inner lumen of hollow struts of the stent, as described in more detail below.

Figure 18:
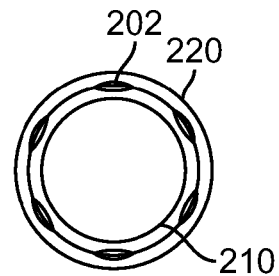

An inner thin-walled 210 tube is inserted into a lumen 204 of tube 200 and a outer thin-walled tube 220 is placed over tube 200, thereby sandwiching tube 200 between tubes 210 and 220, as partially shown in FIG. 17. Tubes 210 and 220 are made from a material desired for the final stent. The material also must be passive with respect to the process used to remove tube 200, as described in more detail below. The three-layer tube is processed so that the walls of tubes 210 and 220 surround struts 202 of tube 200, as shown in FIG. 18. An example of such a process includes inserting a support rod in inner tube 210. A cylindrical press swages or compression welds the three tubes together. Other steps such as alloying can be used to remove latent stresses from the tubes.

Figure 19:
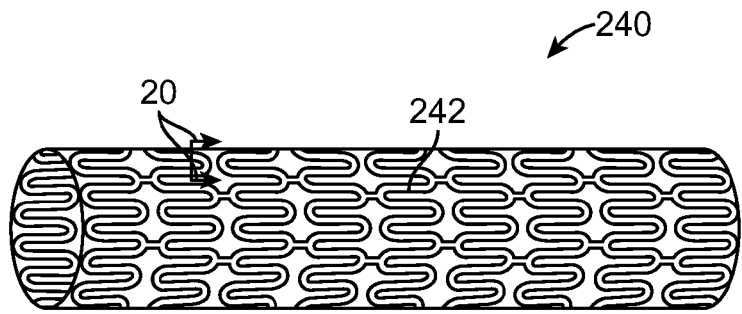
Figure 20:
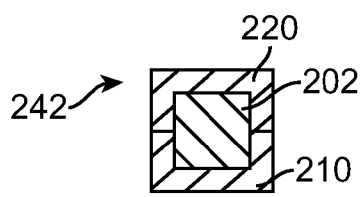
Figure 22:
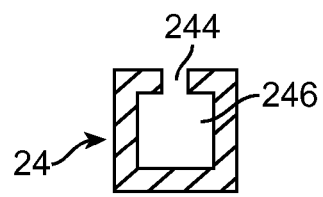

The combined tube is then laser-cut, etched or otherwise processed to remove material such that the remaining material is shaped as stent 240, as shown in FIG. 19. Struts 242 of stent 240 include an outer layer formed from the material of tubes 210 and 220, and an inner layer formed from the struts 202 of tube 200, as shown in FIG. 20.

Figure 21:
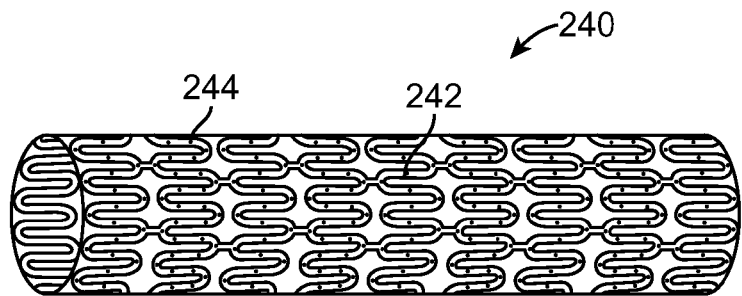

Holes 244 are then laser-cut or otherwise drilled into struts 242, as shown in FIG. 21. Stent 240 is then exposed to a process for removing struts 202 from struts 242. For example, as described above, tube 200 (and hence struts 202) may be made from tungsten, molybdenum, niobium, rhenium, carbon, germanium, or silicon and inner and outer tubes 210, 220 may be made from MP35N. Stent 240 may be exposed to xenon difluoride gas at low pressure and relatively high temperature such that it reacts with struts 202 to form a gas which can be exhausted through holes 244 or other ports cut into stent 240. Xenon difluoride does not react with MP35N. Accordingly, struts 242 remain and a lumen 246 is created in the void where struts 202 were dissolved away. Lumen 246 may then be filled with a therapeutic substance, as explained above. The alternative materials and processes for removing core members discussed below can be used in the process for making a stent described here to remove struts 202 from lumen 246 of struts 242.

The therapeutic substance or drug may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-COA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include nitric oxide, alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Further, a carrier may be used with the therapeutic substance or drug. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the drug and the solvent to aid elution of the drug.

Methods for Removing Core Members from Outer Members

In the stent embodiments described, the hollow tubular structure is formed from a core wire or composite member including an outer member and a core member, wherein the core member is a sacrificial material that is removed after shaping the combined outer member/core member (core wire) into a desired shape. In the embodiments described, the outer member may be formed from a metal such as MP35N and the core member may be formed from tantalum. The core member is exposed to xenon difluoride gas in a vacuum which reacts with the core member material to form a gas that can be exhausted from the outer member. Alternatively, bromine trifluoride ($BrF_3$) or other interhalogen gases can be used instead of xenon difluoride to react with the core member.

Other materials for the core member and the outer member may be used with other gases to react with the core member. For example, nickel (Ni) can be used as a core member and platinum, iridium, titanium, or tantalum can be used as an outer member. The core member is exposed to carbon monoxide (CO), which reacts with the nickel core member to form gaseous nickel carbonyls that is evaporated from the lumen of the outer member. Carbon monoxide does not react with the materials listed as exemplary outer members. In another example, the core member can be made from titanium or zirconium and exposed to iodine ($I_2$). The iodine reacts with the titanium or zirconium core member titanium iodide ($TiI_4$) or zirconium iodide ($ZrI_4$), which may be gases under the proper etching conditions known to those skilled in the art. Outer members formed from materials that do not react with iodine, for example, stainless steel and nickel based alloys, are used.

Other methods may also be used to support the outer member while the core wire is formed into a desired shape or otherwise processed, and to then remove the core member, leaving a hollow tubular structure.

In one embodiment, wet chemical dissolution is used such that the core member is exposed to a chemical that reacts with the core member to dissolve the core member, but does not react with the outer member. Examples of outer member/core member combinations and chemical etchants include, but are not limited to: an MP35N outer member and a molybdenum core member with hydrogen peroxide ($H_2O_2$) as the chemical etchant; a Nitinol (and other nickel alloys) or stainless steel outer member and a gold core member with potassium triiodide ($KI_3$) as the chemical etchant; and an aluminum alloy or stainless steel outer member and a copper core member with nitric acid as the chemical etchant. These examples are illustrative and it would be understood by one skilled in the art that a chemical etchant that reacts with the core member to dissolve the core member but does not react with an outer member that is suitable for use as the medical device could be used in this process.

In another embodiment, the core member is removed from the lumen of the outer member by solubilization. The core wire or composite member includes openings as discussed above. Placing the composite member in a liquid solvent in which the core member material is soluble but the outer member is not soluble will dissolve the core member material. The solvent with the core member material dissolved therein is then drained from the lumen of the outer member. In one non-limiting example, the outer member material is a material commonly used for the medical device application and the lumen of the outer member is filled with salt or wax. After shaping the core wire into the desired shape, the shaped core wire is exposed to water or a non-polar solvent such as hexane, respectively. Core member dissolves in the solvent and is removed from the lumen. In another non-limiting example, the outer member may be made of platinum and the core member may be made of metals that are dissolved by mercury, such as silver, gold, and copper. Similarly, tungsten may be used for the outer member and liquid gallium may be used as the solvent. The core member may be made of materials that are dissolved by liquid gallium, such as aluminum.

In another embodiment, sublimation is used to convert the core member from solid phase to gas phase to remove the core member material from the lumen of the outer member. The core member is formed from a material that when heated in a high vacuum converts from its solid phase to its gas phase. The outer member surrounding the core member is made from a material that does not sublimate or melt at the conditions to which the composite member (combined outer member and core member) is exposed. For example, molybdenum or tungsten may be used as the outer member and chromium may be used as the core member. Heating chromium in a vacuum causes chromium to be vaporized by sublimation below its melting point temperature.

In another embodiment, the core member is made from a material with a lower melting point temperature than the material of the outer member. After the core wire is formed into the desired shape or otherwise processed, the core wire is heated to above the melting point temperature of the core member, but below the melting point temperature of the outer member. The core member melts into its liquid phase and is removed from the lumen of the outer member. The outer member should be selected such that heating the core wire above the melting point temperature of the core member does not negatively affect the physical properties of the outer member. Examples of outer members that may be used include, but are not limited to, titanium, nickel-chromium alloys such as MP35N, stainless steel, tantalum, and tungsten. Examples of core members that melt at lower temperatures than the outer members include, but are not limited to, magnesium, aluminum, zinc, gold, and silver. In one example, a magnesium core member is surrounded by an outer member formed of MP35N. The melting point for magnesium is approximately 650° C., while the melting point for MP35N is 1440° C. Accordingly, heating a core wire or composite member formed from an outer member formed from MP35N and a core member formed from magnesium to above 650° C., but below 1440° C., melts the magnesium core member into a liquid which can be drained from the lumen of the outer member, leaving a hollow wire. In such an example, the composite member may alternatively be heated above 1090° C., the boiling point of magnesium, but below 1440° C., such that the magnesium core member evaporates from the lumen of the MP35N outer member, leaving a hollow wire.

Bone Screw Embodiments

Figure 23:
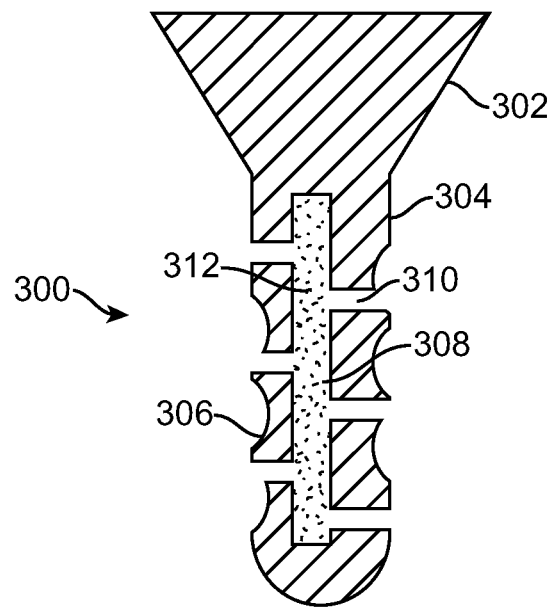
FIG. 23 is a cross-sectional view of a hollow, drug-eluting bone screw in accordance with an embodiment hereof.

FIG. 23 shows a cross-sectional view of a bone screw 300 in accordance with an embodiment hereof. Bone screw 300 includes a head 302 and a shank 304 including threads 306. Bone screw 300 further includes a reservoir or lumen 308 disposed within shank 304. Although reservoir 308 is shown only in shank 304, reservoir 208 can extend into head 302. Holes or openings 310 are provided in shank 304 from an outer surface of shank 304 to reservoir 308. A therapeutic substance or drug 312 is deposited within reservoir 308 such that therapeutic substance 312 elutes from reservoir 308 through holes 310 when bone screw 300 is implanted into a body.

Figure 24:
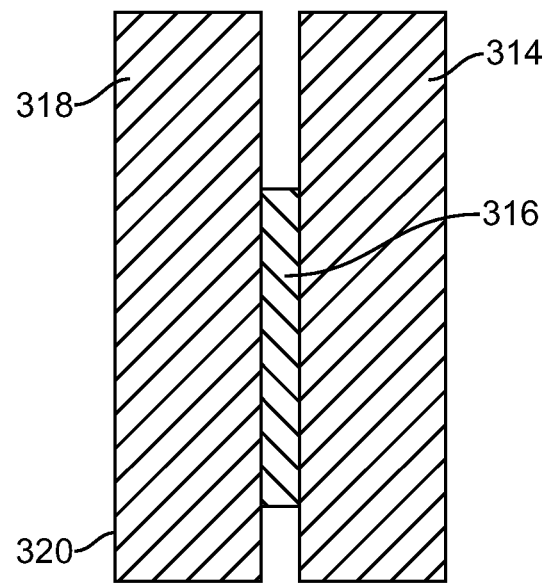
FIGS. 24-28 are cross-sectional views of a method of forming the hollow, drug-eluting bone screw of FIG. 23.

FIGS. 24-28 illustrate an embodiment of a method for making hollow, drug-eluting bone screw 300. As shown in FIG. 24, an outer member 314 is extruded or otherwise provided over a core member 316. Ends 318 and 320 of outer member 314 may extend beyond the ends of core member 316, as shown. Outer member 314 may be formed of any suitable material for a bone screw. Examples of such materials include, but are not limited to, stainless steel, titanium, cobalt, chromium, tungsten, tantalum, molybedenum, and alloys thereof (e.g. MP35N). Core member 316 is formed of a sacrificial material such as those described above. Outer member 314 and core member 316 are selected depending on the process used to dissolve core member 316 from outer member 314, as described above.

Figure 25:
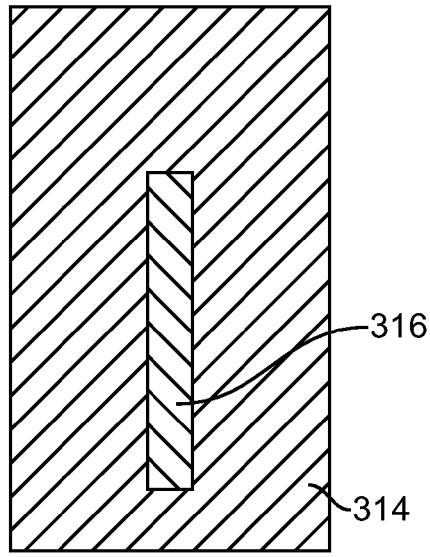
Figure 26:
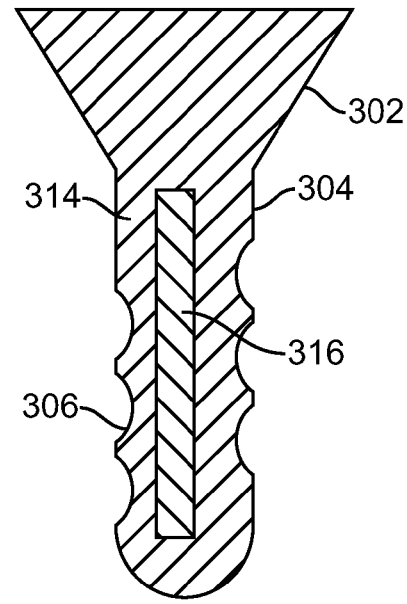
Figure 27:
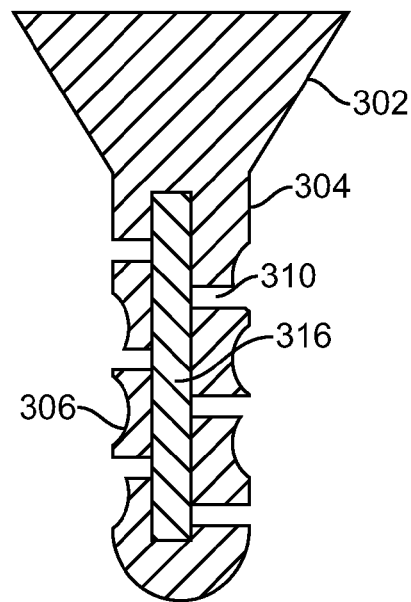
Figure 28:
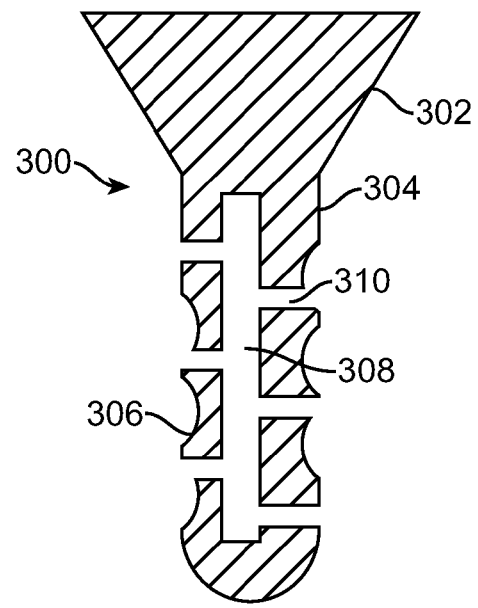

Ends 318, 320 of outer member 314 may then be pressed or otherwise processed such that ends 318, 320 surround core member 316, as shown in FIG. 25. The outer member is then formed into the desired shape using techniques known to those skilled in the art, for example, using a four-axis CNC machine mill. Such process leaves outer member 314 in the shape of bone screw 300 with core member 316 enclosed therein, as shown in FIG. 26. Holes 310 are then drilled, laser cut, or otherwise provided through outer member 314, as shown in FIG. 27. Core member 316 is then exposed to a substance through holes 310 such that core member 316 dissolves and any byproduct material, such as a gas, is exhausted through holes 310, leaving reservoir 308, as shown in FIG. 28. The processes discussed above for removing a core member from an outer member may be used to dissolve core member 316. Reservoir 308 may then be filled with therapeutic substance 312 through holes 310, thereby resulting in bone screw 300 shown in FIG. 24.

Therapeutic substances 312 used in the embodiment described may include, but are not limited to, steroids, antibiotics, anti-inflammatory drugs, anti-proliferative compounds, antimyotic compounds, an antimitotic compounds, antimetabolite compounds, pain-relieving drugs, corticosteroids, angiostatic steroids, non-steroidal anti-inflammatory agents, bone in-growth promoting drugs such as hydroxylapatite and Simvastatin, and other substances as would be apparent to those skilled in the art. Further, carriers or controlled release agents may be added to the therapeutic substance.

Staple Embodiments

FIG. 29 shows a schematic perspective view of a hollow, drug-eluting staple 400 in accordance with an embodiment hereof. Staple includes tips 402 and holes or openings 404 leading to a reservoir or lumen 410 (see FIGS. 33-34). A therapeutic substance or drug 412 (FIG. 34) is deposited within reservoir 410 such that therapeutic substance 412 elutes from reservoir 410 through holes 404 when staple 400 is implanted into a body.

FIGS. 30-34 illustrate an embodiment of a method for making hollow, drug-eluting staple 400. As shown in FIG. 30, an outer member 406 is extruded or otherwise provided over a core member 408. The ends of outer member 406 may extend beyond the ends of core member 408, as shown. Outer member 406 may be formed of any suitable material for a staple. Examples of such materials include, but are not limited to, stainless steel, titanium, cobalt, chromium, tungsten, tantalum, molybedenum, and alloys thereof (e.g. MP35N). Core member 408 is formed of a sacrificial material such as those described above. Outer member 406 and core member 408 are selected depending on the process used to dissolve core member 408 from outer member 406, as described above.

Outer member 406 and core member 408 may be pressed or otherwise processed such that the ends of outer member 406 surround core member 408, and the combination is then formed into the desired shape using techniques known to those skilled in the art. Such processes leaves outer member 406 in the shape of staple 400 with core member 408 enclosed therein, as shown in FIG. 31. Holes 404 are then drilled, laser cut, or otherwise provided through outer member 406, as shown in FIG. 32. Core member 408 is then exposed to a substance through holes 404 such that core member 408 dissolves and any byproduct material, such as a gas, is exhausted through holes 404, leaving reservoir 410, as shown in FIG. 33. The processes discussed above for removing a core member from an outer member may be used to dissolve core member 408. Reservoir 410 may then be filled with therapeutic substance 412 through holes 410, thereby resulting in bone screw 300 shown in FIG. 34.

Therapeutic substances 412 used in the embodiment described may include, but are not limited to, steroids, antibiotics, anti-inflammatory drugs, anti-proliferative compounds, antimyotic compounds, an antimitotic compounds, antimetabolite compounds, pain-relieving drugs, corticosteroids, angiostatic steroids, non-steroidal anti-inflammatory agents, and other substances as would be apparent to those skilled in the art. Further, carriers or controlled release agents may be added to the therapeutic substance.

Implantable Cardioverter Defibrillators

FIG. 35 illustrates an example of a dual chamber, multi-programmable, implantable medical device (IMD) 500 and associated lead system for providing atrial and ventricular sensing functions, based on the programmed pacing and/or sensing mode and providing atrial or ventricular cardioversion therapies.

Depending upon the programmed pacing mode, pacing pulses may be applied to the atrium and/or ventricle in response to the detection of the appropriate bradycardia condition by the IMD 500. The pacing and sensing functions may be effected through atrial and ventricular bipolar pace/sense electrode pairs at the ends of right atrial/superior vena cava (RA/SVC) and right ventricular (RV) leads 502 and 504, respectively. Leads 502 and 504 may be fixed in the right atrium 506 and right ventricle 508, respectively, that are electrically coupled to the circuitry of IMD 500 through a connector block 510.

A coronary sinus (CS) lead 512 includes an elongated insulating lead body enclosing one elongated coiled wire conductor coupled to an elongated exposed coil wire CS cardioversion electrode 514. CS cardioversion electrode 514, illustrated in broken outline, is located within the coronary sinus of the heart 516. At the proximal end of CS lead 512 is a connector end 518 having an exposed connector coupled to the coiled wire conductor and attached within the connector block 510 to connector block terminals in a manner well known in the art.

The RA/SVC lead 502 may include an elongated insulating lead body carrying concentric, electrically isolated, coiled wire conductors separated from one another by tubular insulating sheaths. The lead body may be in an atrial J-shape in order to position its distal end in the right atrial appendage. An atrial pace/sense ring electrode 520 and an extendable helical, pace/sense electrode 522, mounted retractably within an insulating electrode head 524, are formed distally to the bend of the J-shape. Helical electrode 522 is extendable out of the electrode head 524 and can be screwed into the atrial appendage in a manner well known in the art.

RA pace/sense electrodes 520, 522 are employed for atrial pacing and for near-field sensing of P-waves. An elongated, exposed coil, RA/SVC cardioversion electrode 526 is supported on RA lead 502 extending proximally to pace/sense ring electrode 520 and coupled to the third coiled wire conductor within the RA lead body. RA/SVC cardioversion electrode 526 preferably is 10 cm in length or greater and is configured to extend from within the SVC and toward the tricuspid valve 528. At the proximal end of the RA lead 502 is a bifurcated connector 530 which carries three exposed electrical connectors, each coupled to one of the coiled wire conductors, that are attached within the connector block 510 to connector block terminals in a manner well known in the art.

The delivery of atrial cardioversion/defibrillation therapies to the atria may be effected through selected combinations of intracardiac electrodes, e.g. the illustrated exemplary RA/SVC cardioversion electrode 526 and the CS cardioversion electrode 514. The exposed surface 532 of the outer housing or can of the IMD 500 may be selectively used as a can electrode 534. Can electrode 534 may serve as a subcutaneous remote cardioversion electrode in combination with one or more intracardiac cardioversion electrodes for cardioverting or defibrillating the atria.

The RV lead 504 may include an elongated insulating lead body, enclosing at least three concentric, electrically isolated, coiled wire conductors, separated from one another by tubular insulating sheaths. Located adjacent the distal end of the RV lead 504 are a pace/sense ring electrode 536, and a helical, pace/sense electrode 538, mounted retractably within an insulating electrode head 540. Helical electrode 538 is extendable out of the electrode head 540 and can be screwed into the ventricular apex in a manner well known in the art. RV pace/sense electrodes 536, 538 are each coupled to a coiled wire conductor within the RV lead body and are employed for cardiac pacing in the ventricle and for sensing near-field R-waves.

In embodiments of the present invention, implemented to delivering ventricular cardioversion therapies, a distal segment of RV lead 504 also supports an elongated, exposed wire coil, cardioversion electrode 542. Cardioversion electrode 542 may be placed in the right ventricle 508 of heart 516 and connected to a further coiled wire conductor within the RV lead body. Although not specifically illustrated, it will be understood that the ventricular cardioversion therapies may be delivered between further RV cardioversion electrodes in combination with cardioversion electrode 542 or between the cardioversion electrode and the can electrode 534 and/or the CS cardioversion electrode 514 or the RA/SVC cardioversion electrode 526. At the proximal end of the RV lead 504 is a bifurcated connector end 544 having a plurality of electrical connectors, each coupled to one of the coiled conductors in the RV lead body, that are attached within the connector block 510 to connector block terminals in a manner well known in the art.

Helical electrodes such as helical electrode 538 are placed into the heart tissue, and deliver the electrical stimulation to the heart. An embodiment a helical or spiral electrode 538 is shown in FIGS. 36 and 37. Electrode 538 includes a lumen 552 disposed therethrough and including a therapeutic substance 554 disposed therein. Holes or openings 550 disposed through an outer member 556 allow therapeutic substance 556 to elute to the targeted tissue. Electrode 538 may be formed as described above, that is: by forming a core wire formed of outer member 556 and a core member (not shown); shaping the core wire into the desired shaped; drilling or laser-cutting openings 550 through outer member 556; exposing the core member to an etchant such that the core member dissolves; and filling lumen 552 with therapeutic substance 554. Outer member can be any material that is commonly used for electrodes, such as stainless steel, MP35N, and platinum/iridium alloys. The core member is made from a sacrificial material and is selected based on the method used to dissolve the core member and the material selected for outer member 556.

Therapeutic substance 552 may include, but is not limited to, anti-inflammatory drugs such as steroids, antibiotics, and anti-fungal materials. Further, carriers or controlled release agents may be added to the therapeutic substance.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a medical device comprising the steps of:
    forming an outer member over a core member, wherein the outer member has an outer surface and an inner surface, the inner surface defining an outer member lumen such that the core member is disposed within the outer member lumen, the outer and core members forming an elongate composite wire;
    shaping the composite wire into a pattern by bending the composite wire into a waveform, wherein the pattern defines a stent lumen;
    forming openings through the outer member; and
    after the step of shaping the composite wire into the pattern, exposing the composite wire to an etchant that reacts with the core member to remove the core member from the outer member without adversely affecting the outer member.

2. The method of claim 1, further comprising the step of filling the lumen of the outer member with a therapeutic substance after the core member has been removed.

3. The method of claim 2, wherein the therapeutic substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

4. The method of claim 1, wherein the etchant is a liquid chemical that dissolves the core member.

5. The method of claim 4, wherein the outer member is formed from MP35N, the core member is formed from molybdenum, and the etchant is hydrogen peroxide.

6. The method of claim 4, wherein the outer member is formed from a nickel titanium alloy or stainless steel, the core member is formed from gold, and the etchant is potassium triiodide.

7. The method of claim 4, wherein the outer member is formed from an aluminum alloy or stainless steel, the core member is formed from copper, and the etchant is nitric acid.

8. The method of claim 1, wherein the etchant is a gas.

9. The method of claim 8, wherein the outer member is formed from MP35N, the core member is formed from one of tantalum, tungsten, molybdenum, niobium, rhenium, carbon, germanium, and silicon, and the etchant is xenon difluoride.

10. The method of claim 8, wherein the outer member is formed from MP35N, the core member is formed from one of tantalum, tungsten, molybdenum, niobium, rhenium, carbon, germanium, and silicon, and the etchant is bromine trifluoride.

11. The method of claim 8, wherein the outer member is formed from the group consisting of platinum, iridium, titanium, and tantalum, the core member is formed from nickel, and the etchant is carbon monoxide.

12. The method of claim 8, wherein the outer member is formed from stainless steel or nickel-based alloys, the core member is formed from titanium or zirconium, and the etchant is iodine.

13. The method of claim 1, wherein the core member is soluble in the etchant and the outer member is not soluble in the etchant.

14. The method of claim 13, wherein the outer member comprises platinum, the core member is selected from the group consisting of silver, gold, and copper, and the etchant comprises mercury.

15. The method of claim 13, wherein the outer member comprises tungsten, the core member comprises aluminum, and the etchant comprises liquid gallium.

16. The method of claim 1, wherein the step of shaping the composite wire comprises helically wrapping the waveform around a mandrel.

17. A method of forming a medical device comprising the steps of:
    shaping a composite member into a pattern, the composite member including an outer member formed from MP35N and a core member disposed within a lumen of the outer member, wherein the core member is formed from one of tantalum,
    tungsten, molybdenum, niobium, rhenium, carbon, germanium, and silicon; forming openings through the outer member; and after the step of shaping the composite member into the pattern, processing the composite member such that the core member is removed from the outer member without adversely affecting the outer member, wherein the step of processing the composite member comprises exposing the composite member to a xenon difluoride gas that reacts with the core member to remove the core member, wherein the xenon difluoride gas does not react with the outer member.

18. The method of claim 17, further comprising the step of filling the lumen of the outer member with a therapeutic substance after the core member has been removed.

19. The method of claim 18, wherein the therapeutic substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

20. The method of claim 18, wherein the medical device is a stent.

* * * * *